(12) United States Patent
Sadeghian Marnani

(10) Patent No.: US 11,774,381 B2
(45) Date of Patent: Oct. 3, 2023

(54) METHOD FOR MEASURING DAMAGE OF A SUBSTRATE CAUSED BY AN ELECTRON BEAM

(71) Applicant: Nederlandse Organisatie voor toegepast-natuurwetenschappelijk onderzoek TNO, 's-Gravenhage (NL)

(72) Inventor: Hamed Sadeghian Marnani, The Hague (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 959 days.

(21) Appl. No.: 16/325,995

(22) PCT Filed: Aug. 30, 2017

(86) PCT No.: PCT/NL2017/050572
§ 371 (c)(1),
(2) Date: Feb. 15, 2019

(87) PCT Pub. No.: WO2018/044164
PCT Pub. Date: Mar. 8, 2018

(65) Prior Publication Data
US 2021/0333226 A1   Oct. 28, 2021

(30) Foreign Application Priority Data

Aug. 31, 2016 (EP) .................................... 16186519

(51) Int. Cl.
*G01N 23/2251* (2018.01)
*G01Q 60/38* (2010.01)

(52) U.S. Cl.
CPC ......... *G01N 23/2251* (2013.01); *G01Q 60/38* (2013.01); *G01N 2223/07* (2013.01); *G01N 2223/507* (2013.01)

(58) Field of Classification Search
CPC .......... G01N 23/2251; G01N 2223/07; G01N 2223/507; G01N 29/0681; G01N 29/12;
(Continued)

(56) References Cited

U.S. PATENT DOCUMENTS 5,253,516 A * 10/1993 Elings .................... G01Q 70/02
                                                            73/105
5,386,720 A *  2/1995 Toda ...................... B82Y 35/00
                                                            73/105

(Continued)

OTHER PUBLICATIONS

Rabe, U., et al. "Quantitative determination of contact stiffness using atomic force acoustic microscopy." Ultrasonics 38.1-8 (2000): 430-437 (Year: 2000).*

(Continued)

*Primary Examiner* — David E Smith
(74) *Attorney, Agent, or Firm* — Leydig, Voit & Mayer, Ltd.

(57) ABSTRACT

A method for measuring damage (D) of a substrate (1) caused by an electron beam (2). The method comprises using an atomic force microscope (AFM) to provide a measurement (S2) of mechanical and/or chemical material properties (P2) of the substrate (1) at an exposure area (1a) of the electron beam (2). The method further comprises calculating a damage parameter (Sd) indicative for the damage (D) based on the measurement (S2) of the material properties (P2) at the exposure area (1a).

13 Claims, 4 Drawing Sheets

(58) Field of Classification Search
CPC ..... G01N 2033/0095; G01N 2291/014; G01N 2291/02827; G01N 2291/0427; G01N 29/043; G01Q 60/38; G01Q 30/02; G01Q 60/32; G01Q 60/24; G01Q 90/00
See application file for complete search history.

(56) References Cited

U.S. PATENT DOCUMENTS

| | | | | |
|---|---|---|---|---|
| 9,466,463 | B1* | 10/2016 | Lam | H01J 37/3045 |
| 2008/0141764 | A1* | 6/2008 | Takaoka | G01N 23/2251 |
| | | | | 73/105 |
| 2008/0276695 | A1* | 11/2008 | Prater | G01N 29/0681 |
| | | | | 73/105 |
| 2012/0228494 | A1* | 9/2012 | Kuan | G03F 1/86 |
| | | | | 250/307 |

OTHER PUBLICATIONS

Stevens et al, "Nanoscale Electron Beam Damage Studied by Electron Beam Microscopy", The Journal of Physical Chemistry C 113.43 (2009 (Year: 2009).*

Harnett et al., "Low-Energy Electron-Beam Patterning of Amine-Functionalized Self-Assembled Monolayers," Applied Physics Letters, American Institute of Physics Publishing LLC US, vol. 76, No. 17, pp. 2466-2468 (Apr. 24, 2000) XP012025152.

Mowatt et al., "A Study of Dynamic SIMS Analysis of Low-K Dielectric Materials," Applied Surface Science, vol. 252, No. 19, pp. 7182-7185 (Jul. 30, 2006) XP024892975.

Cheng et al., "Damage-Free Metrology of Porous Low-K Dielectrics Using CD-SEM," Metrology, Inspection, and Process Control for Microlithography XVIII, edited by Richard M. Silver, Proceedings of SPIE vol. 5375, pp. 665-674 (May 24, 2004) XP040182490.

European Patent Office, International Search Report in corresponding International Application No. PCT/NL2017/050572 dated Mar. 20, 2018 (3 pages).

Sam M. Stevens et al., "Nanoscale Electron Beam Damage Studied by Atomic Force Microscopy," The Journal of Physical Chemistry C Letters, vol. 113, No. 43, pp. 18441-18443 (2009) Published on the Web Oct. 7, 2009.

U. Rabe et al., "Quantitative determination of contact stiffness using atomic force acoustic microscopy," Elsevier, Ultrasonics, No. 38 (2000) pp. 430-437.

Korean Patent Office, Office Action in corresponding Korean Application No. 10-2019-7009299 dated Feb. 23, 2023.

A.F. Sarioglu et al., "Modeling the Effect of Subsurface Interface Defects on Contact Stiffness for Ultrasonic Atomic Force Microscopy," Applied Physics Letters vol. 84, No. 26, pp. 5368-5370 (Jun. 28, 2004).

* cited by examiner

METHOD FOR MEASURING DAMAGE OF A SUBSTRATE CAUSED BY AN ELECTRON BEAM

CROSS-REFERENCE TO RELATED APPLICATIONS

This patent application is a U.S. National Phase of PCT International Application No. PCT/NL2017/050572, filed Aug. 30, 2017, which claims priority to European Application No. 16186519.1, filed Aug. 31, 2016, which are both expressly incorporated by reference in their entireties, including any references contained therein.

TECHNICAL FIELD AND BACKGROUND

The present disclosure relates to a method wherein an electron beam interacts with a substrate, in particular to a method for measuring any substrate damage that may be caused as a result of the electron beam interaction.

For example, scanning electron microscopy (SEM) or electron beam (ebeam) inspection are used in semiconductor industry for metrology and inspection, e.g. critical dimension (CD-SEM) or defect review (DR-SEM) measurements. Current challenges for ebeam inspection and SEM metrology may include for example:

1. Ever smaller feature sizes (e.g. below 10 nm) and increasing complexity of device design (e.g. 3D).
2. Application of new materials such as low k (stiffness), new resist, etcetera which can be very electron sensitive and cause shrinkage or other damage to the materials, especially those for which increasing the resolution higher electron energy is needed.
3. Introduction of new inspection methods by electron beams employing higher electron energy which allows the electrons to penetrate deeper for looking through some layers, but may also increase damage to sensitive layers.

These and other challenges make it important to accurately measure the level of damage to the device or layers when electron beams are being used. For example, Stevens at el. (J. Phys. Chem. Lett. 2009, 113, 18441-18443) describes Nanoscale Electron Beam Damage Studied by Atomic Force Microscopy (AFM). This paper discloses that there is a correlation between the depth of a depression (difference in height between the damaged and undamaged surface) created by the beam damage with both time of exposure and probe current. However, not all types of damage may be correlated to a changing surface topology, especially when the damage occur deeper below the surface.

It is desired to provide a more accurate method for measuring damage of a substrate caused by an electron beam, also below the surface.

SUMMARY

In one aspect, the present disclosure provides a method for measuring damage of a substrate caused by an electron beam. The method comprises using an atomic force microscope to provide a measurement of mechanical and/or chemical material properties of the substrate at an exposure area of the electron beam. Based on the measurement of the material properties at the exposure area calculating a damage parameter may be calculated which is indicative for the damage. For example, the damage parameter is calculated based on material properties including adhesive and/or viscoelastic material properties.

It will be appreciated that the measurement of material properties by an AFM may reveal electron-induced changes to the substrate that are not otherwise detectable, e.g. do not necessarily manifest as changes to the topology (height) at the substrate surface. For example material properties such as adhesiveness, friction, viscosity and/or elasticity may be critically changed even if the height of the substrate surface is relatively unaffected. Advantageously, the inventors find that the measurement of such material properties can be more sensitive than the measurement of only topology changes. Without being bound by theory, this may be because the changes in mechanical and/or chemical material properties caused by an electron beam only manifest as topology changes (e.g. indentations) in some cases where the damage is severe and concentrated. Accordingly, the present methods may provide a more accurate method for measuring damage of a substrate caused by an electron beam than topology measurements.

In some embodiments, the damage parameter is calculated based on a comparison of the material properties at the exposure area with reference properties measured at an unexposed area where the electron beam has not interacted with the substrate. For example, the reference properties of an unexposed area are measured at the exposure area before applying the electron beam. Alternatively, or in addition, reference properties of an unexposed area may be measured at a reference area not overlapping the exposure area. Alternatively, or in addition, the damage parameter is calculated based on a comparison of the material properties of the exposure area with predetermined reference properties. By comparing the damage parameter of exposed areas with that of an unexposed area or with predetermined reference properties, any changes caused by the electron beam can be easily quantified. For example a damage severity is calculated by comparison of the damage parameter with a predetermined threshold difference between the material properties of the exposure area and reference properties, e.g. of an unexposed area or predetermined.

Material properties indicative for substrate damage can be measured using various AFM techniques. In one embodiment, the present methods include force-distance measurements. For example, a force-distance curve can be obtained by varying a distance between the AFM tip and the substrate surface while measuring a corresponding force at each distance. Typically, the curve may follow a different path depending on whether the tip approaches or retracts from the substrate surface. For example, a directional coefficient or derivative of the curve, e.g. at its maximum value or otherwise, may be used as a measure for elasticity or stiffness of the material at the area under the AFM tip. For example, a negative (pulling) force that occurs while retracting the tip from the surface, this be used as a measure for an adhesive property of the material at the area under investigation. For example, a distance that the tip can be (reversibly) pressed into the substrate surface, may be used as a measure for a deformation property (deformability) of the material at the area under investigation. For example, a maximum force in the curve as the tip presses into the substrate surface may be uses as a measure for a peak force property of the material at the area under investigation. For example, an area between the curves for approaching and retracting the tip may be used as a measure for a viscosity or energy dissipation property of the material at the area under investigation. Also other characteristics of a force-distance curve, or combination of characteristics can be used as measure for material properties.

Damage caused by the electron beam may not be limited to the substrate surface, e.g. manifest additionally or exclusively as damage inside the substrate below the exposure area. Accordingly, in some embodiments the AFM may be configured to measure subsurface material properties. For example, the atomic force microscope may be combined with an ultrasound generator. Ultrasound waves traversing the substrate may interact with subsurface features. This interaction can be measured by an AFM coupling to the surface, e.g. via contact between the tip and surface. For example, ultrasound waves in the substrate are coupled via an AFM tip to an AFM cantilever causing vibration of the AFM cantilever.

In some embodiments, the damage parameter is calculated based on measurement of a contact stiffness or wave scattering of the atomic force microscope at the exposure area. For example, a vibrational amplitude of the AFM cantilever depends on a contact stiffness of the AFM tip contacting the substrate. In some embodiments, the contact stiffness may be indicative for the material properties at and/or below the substrate surface. For example, the damage parameter may be based on a measurement of vibrational amplitude of the AFM cantilever.

In some embodiments, a contact resonance frequency of the AFM cantilever while the AFM tip contacts the substrate is a measure for the material properties of the substrate at or below the surface. Other or further embodiments may include heterodyne force microscopy, atomic force acoustic microscopy or force modulation microscopy. In some embodiments, ultrasound waves through the substrate are modulated by a modulation frequency near a contact resonance frequency of the AFM. For example, the modulation frequency near the contact resonance frequency causes an amplitude increased of the AFM cantilever vibrations by a factor of two or more compared to an off-resonant vibration of the AFM cantilever. The contact resonance frequency may shift depending whether the AFM tip contacts an exposure area of the electron beam or an unexposed area of the substrate. Accordingly, a shifting of the contact resonance frequency may causes an amplitude difference of the cantilever vibrations caused by the ultrasound waves between the exposure area and the unexposed area. The amplitude difference can be used in some embodiments for calculating the damage parameter.

Further aspects of the present disclosure may provide an improved method for metrology or inspection of a substrate. In one embodiment, the method comprises performing the metrology or inspection by means of an electron beam directed at an exposure area of the substrate and applying the method as described herein for measuring any damage of the substrate caused by the electron beam at the exposure area. For example, the measured damage may be compared to a threshold and a decision is taken on keeping or discarding the substrate depending on the comparison.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1A:
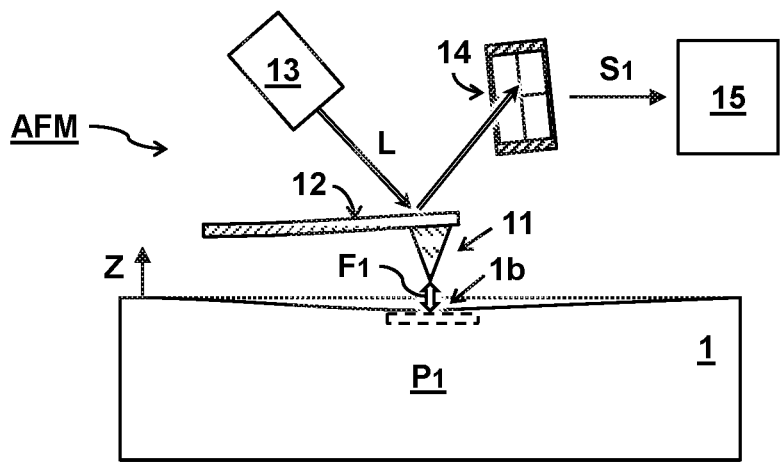
FIGS. 1A-1C schematically shows steps of an embodiment for measuring electron beam damage using an AFM.

In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 1B:
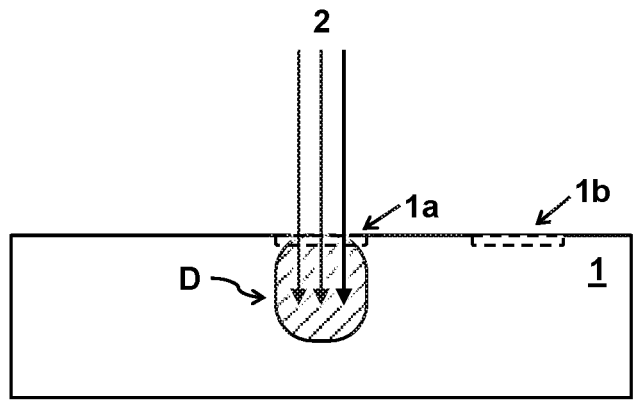
Figure 1C:
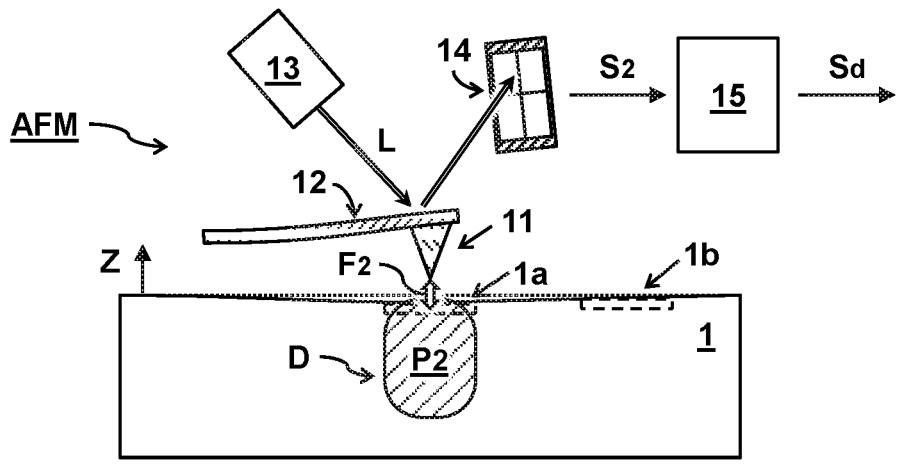

FIGS. 1A-1C schematically shows a method for measuring damage D of a substrate 1 caused by an electron beam 2 using an atomic force microscope (AFM). FIG. 1A shows the AFM providing a measurement S1 of mechanical and/or chemical material properties P1 at an unexposed region 1*b* of the substrate. FIG. 1B shows the electron beam 2 interacting with the substrate 1 causing damage D at the exposure area 1*a*. FIG. 1C shows the AFM providing a measurement S2 of mechanical and/or chemical material properties P2 of the substrate 1 at the exposure area 1*a* of the electron beam 2. Based on the measurement S2 of the material properties P2 at the exposure area 1*a*, a damage parameter Sd is calculated which is indicative for the damage D.

In one embodiment, the damage parameter Sd is calculated based on a comparison of the material properties P2 at the exposure area 1a with reference properties P1 measured at an unexposed area where the electron beam 2 has not interacted with the substrate 1. For example, reference properties P1 of an unexposed area are measured at the exposure area before applying the electron beam. Alternatively, or in addition, reference properties P1 of an unexposed area are measured at a reference area 1b not overlapping the exposure area 1a. Alternatively, or in addition, the damage parameter Sd is calculated based on a comparison of the material properties P2 of the exposure area with predetermined reference properties P1. In some embodiments, a damage severity is calculated by comparison of the damage parameter Sd with a predetermined threshold difference between the material properties P2 of the exposure area 1a and reference properties P1. For example, the severity of the damage may determine whether the substrate 1 is discarded.

In some aspects, the present methods and systems may be used for metrology or inspection of a substrate. In one embodiment, such methods comprise performing the metrology or inspection by means of an electron beam 2 directed at an exposure area of the substrate 1 and applying the methods as described herein for measuring any damage D of the substrate 1 caused by the electron beam 2 at the exposure area 1a. For example, the measured damage D may be compared to a threshold and the substrate 1 is either kept or discarded for subsequent processing depending on the comparison.

In the embodiment shown, a laser source 13 provides a laser beam L that impinges on the cantilever 12 and reflects towards an optical detector 14. Using the optical detector 14, vibrations in the cantilever 12 can be sensed due to small deflections of the reflected beam L under influence of such vibrations. This provides an output signal 26 for further analysis, e.g. by a processor 15 to calculate the damage parameter Sd. In some embodiments, the processor 15 may comprise a memory to store previous measurements S1 or reference values for comparison.

Alternative or in addition to measuring beam deflection also other ways may be envisaged for measuring the cantilever deflection and/or vibration frequency/amplitude. Alternative sensing techniques for example include the application of a piezo-resistive layer, the electrical resistance of which vary with probe deflection. Probe deflection may in that case be detected by detecting voltage differences in an electric signal applied to the piezo-resistive layer. As another alternative, probe deflection may be detected using a piezo-electric element or layer, the potential of which changes dependent on cantilever motion. Alternatively, capacitive measurements may be applied in an electrostatic sensing technique. As some further alternatives, one may also apply an interferometer to measure probe deflection or perform a heat flux measurement in a thermal method by using a temperature difference between probe and substrate. The skilled person will be familiar with such techniques and is able to apply them in embodiments of the present invention.

Figure 2:
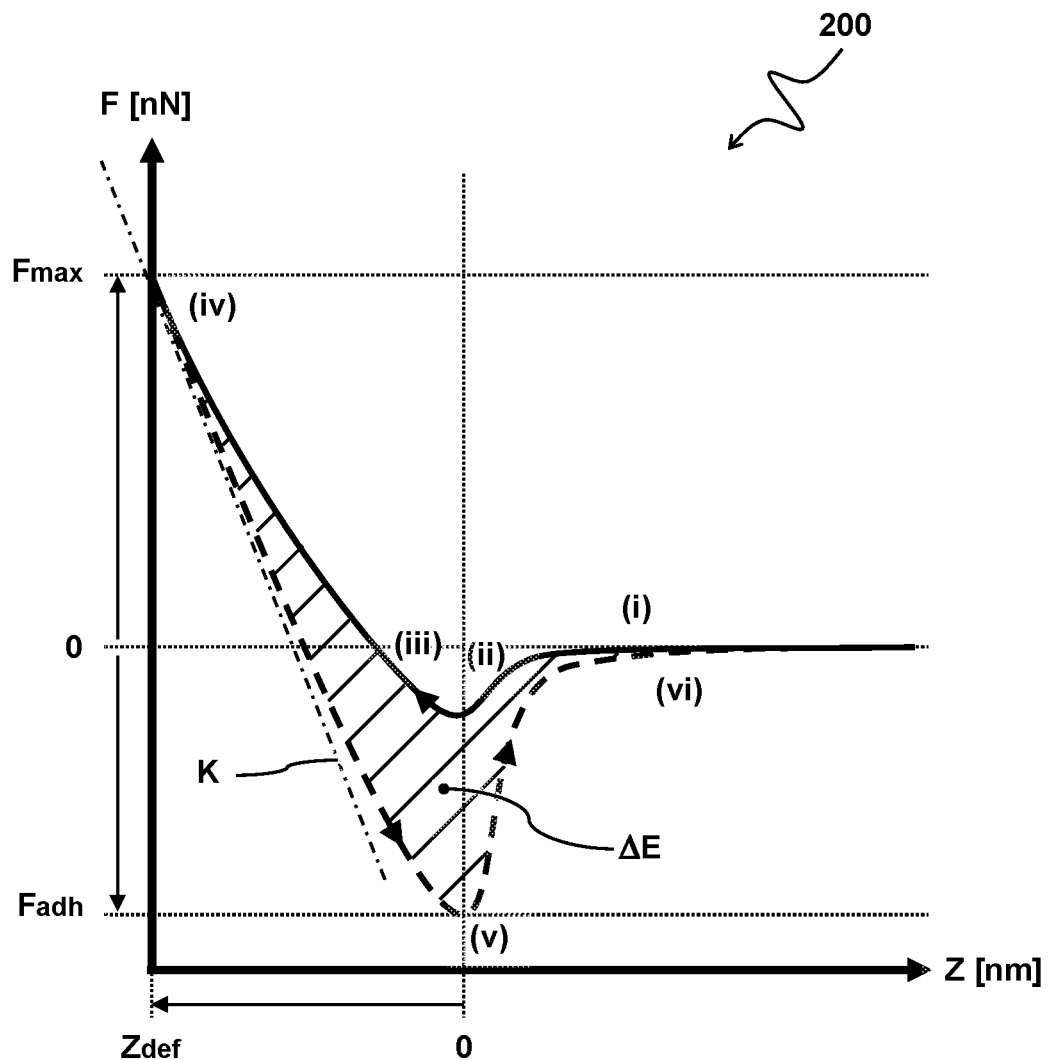
FIG. 2 schematically shows a force distance curve (top) in various phases of an AFM tip approaching and retracting from the substrate (bottom)
Figure 2:
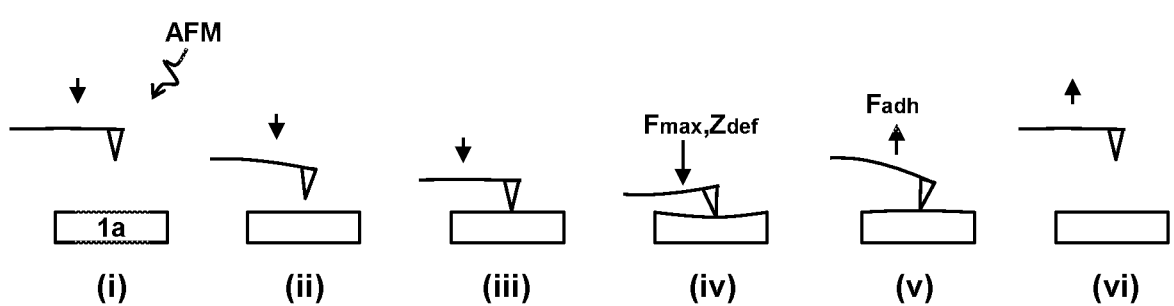

FIG. 2 schematically shows a force distance curve 200 in various phases (i)-(vi) of an AFM tip first approaching and then retracting from the substrate (shown on the bottom).

In phase (i), the AFM tip start at a distance from the surface where interaction forces with the substrate are negligible. As the AFM tip approaches the surface in phase (ii), the AFM tip is attracted to the surface e.g. by Van-der-Waals-forces. This may cause deflection of the AFM cantilever towards the substrate registered here as a negative force. As the AFM tip is brought even closer to the surface in phase (iii), repulsive interactions, e.g. ionic or Pauli-repulsion, start to play a role. The repulsive forces at some point counteract the attractive forces and may increase to maximum force in phase (iv). At this point, the movement may be reversed and the AFM tip retracted from the surface. As the tip retracts it may experience adhesive force caused by the AFM tip sticking to the surface in phase (v). Finally, as the AFM tip is pulled further away, the distance can be increased in phase (vi) until the interaction forces are again negligible.

Figure 3:
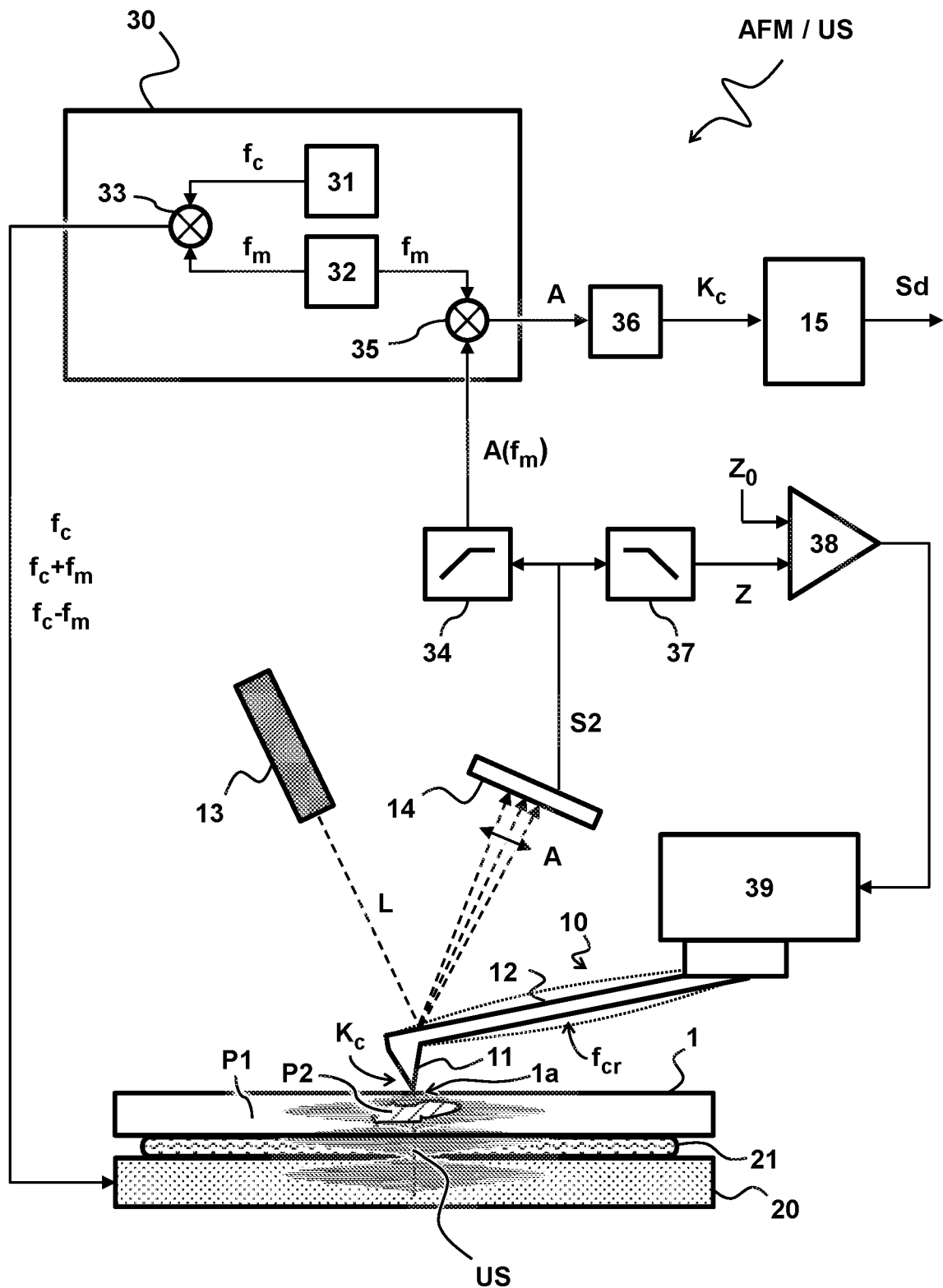
FIG. 3 schematically shows an embodiment of an ultrasound AFM for measuring subsurface material properties.

In some embodiments a damage parameter is calculated based on material properties including adhesive and/or viscoelastic material properties. For example, material properties are calculated based on a force-distance measurement 200 of the atomic force microscope AFM, as shown, or otherwise. In one embodiment, the damage parameter is calculated based on an elasticity or stiffness K of the exposure area 1a. In another or further embodiment, the damage parameter is calculated based on an adhesive property Fadh of the exposure area 1a. In another or further embodiment, the damage parameter is calculated based on a deformation property Zdef of the exposure area 1a. In another or further embodiment, the damage parameter is calculated based on a peak force property Fmax of the exposure area 1a. In another or further embodiment, the damage parameter is calculated based on a viscosity or energy dissipation property $\Delta E$ of the exposure area 1a. In another or further embodiment, FIG. 3 schematically shows an embodiment of an AFM system comprising an ultrasound generator 20 configured to generate ultrasound waves (US) in the substrate 1.

In the shown embodiment of the AFM, a probe 10 is attached to a scan head 39. The scan head 39 enables scanning of the probe 10 relative to a surface of substrate 1. The probe 10 consists of a cantilever 12 and a probe tip 11. During scanning, the probe tip 11 is brought in contact with the surface of the substrate 1. For example the probe tip 11 may be scanned across the surface of the substrate 1 in contact mode (continuous contact between the probe tip 11 and the surface of the substrate 1) or tapping mode (periodic contact between the probe tip 11 and the surface of the substrate 1 during each cycle of a vibration applied to the cantilever 12).

In some embodiments, the AFM is configured to measure subsurface material properties P1, P2 below unexposed or exposed surface areas of the substrate 1. In one embodiment, the AFM tip 11 is brought in contact with the area under investigation 1a. In another or further embodiment, the damage parameter Sd is calculated based on measurement of a contact stiffness Kc of the atomic force microscope AFM at the exposure area 1a. Typically, ultrasound waves US in the substrate 1 may be coupled via the AFM tip 11 to the AFM cantilever 12 causing vibration of the AFM cantilever 12. For example, a vibrational amplitude "A" of the AFM cantilever 12 may depend on a contact stiffness Kc of the AFM tip 11 contacting the substrate 1. Contact stiffness Kc may be quantified e.g. as the combined stiffness of the tip contacting the substrate, e.g. derivate of a force experienced by the tip as a function of displacement of the tip. It will be appreciated that the contact stiffness Kc may depend on material properties P2 below the substrate 1 surface. In turn, the contact stiffness may determine vibrational modes in the AFM cantilever 12.

In some embodiments a contact resonance frequency "fcr" of the AFM cantilever 12 may depend on the contact stiffness Kc. Accordingly, a contact resonance frequency "fcr" of the AFM cantilever 12 while the AFM tip 11 contacts the substrate 1 can be a measure for the material properties P2 of the substrate 1 at or below the surface. The contact resonance frequency "fcr" may be probed e.g. by including a modulation frequency "fm" in the ultrasound waves US through the substrate 1. Alternatively, or in addition, ultrasound waves may be generated at the tip (not shown), or both at the tip and the sample simultaneously (not shown). For example, the ultrasound waves US can be modulated by a modulation frequency "fm" near a contact resonance frequency "fcr" of the AFM. The closer the modulation frequency "fm" is to the contact resonance frequency "fcr", the higher the amplitude "A" of the resulting vibration in the AFM cantilever 12 at that frequency. Accordingly, in some embodiments, the damage parameter Sd may be based on a measurement S2 of vibrational amplitude "A" of the AFM cantilever 12.

In addition to the modulation frequency "fm", the ultrasound waves US may comprise other signal components, e.g. a carrier frequency "fc". For example, the carrier frequency "fc" can be a relatively high frequency determining interaction with the substrate material while the modulation frequency "fm" is at a relatively low frequency near a contact resonance frequency of the cantilever. For example, the carrier frequency "fc" is more than 10 MHz, e.g. between 20 and 100 MHz. For example, the modulation frequency "fm" is lower than the carrier frequency "fc", e.g. by a factor of at least ten, e.g. between 10 kHz and 5 MHz. Of course also other frequencies can be envisaged depending on the particulars of the system under investigation and/or intrinsic properties of the cantilever.

Ultrasonic force microscopy may for example performed by applying an ultrasonic signal to the substrate and modulating the ultrasonic wave with a modulation frequency "fm" of approximately the cantilever resonance frequency. By sensing the output signal at the modulation frequency and analyzing the amplitude and/or phase, subsurface structures can be imaged. Without being bound by theory, this may be explained by the fact that the high frequency (fc) ultrasonic signal may be perturbed by the subsurface structures. Information on the subsurface structures is conveyed via these perturbations and becomes measureable in the deflection of the probe tip, i.e. the output sensor signal at or near the cantilever resonance frequency.

In the embodiment shown, a signal generation and analysis system 30 is used to generate and extract signals. A first signal generator 31 provides a first signal at the carrier frequency "fc". A second signal generator 32 provides a second signal at the modulation frequency "fm". The frequencies may serve as input for a mixer 33 which generates mixed signals e.g. providing three frequency components: the carrier frequency fc, the carrier frequency fc lowered by the modulation frequency "fm" to obtain a frequency component fc-fm, and the carrier frequency fc increased by the modulation frequency "fm" to obtain a frequency component fc+fm. For example, offering these frequency component signals in a favorable signal component ratio (e.g. fc:(fc−fm):(fc+fm)=1:0.5:0.5) may yields an amplitude modulated wave having a frequency "fc" wherein the amplitude modulates at a frequency "fm".

In the embodiment shown, a single ultrasound generator 20 (transducer) is shown to generate ultrasound waves US at a particular set of frequencies. Alternatively, or in addition, multiple ultrasound generators (not shown) can be used in homodyne or heterodyne configuration. For example an additional frequency may be applied directly to the AFM probe, e.g. by a modulated laser beam L or otherwise. Furthermore, signals may be generated at alternative or additional frequencies than shown or only at a single (modulation) frequency. In some embodiments, the signals may be amplified in a power amplifier (not shown) before being provided to the generator 20. In the shown embodiment, a coupling medium 21 (e.g. water) is used to provide for acoustic coupling between the generator 20 and the substrate 1. In alternative embodiments this may be omitted. In the shown embodiment, the ultrasound generator 20 is below the substrate 1. This has an advantage that the ultrasound waves US are affected by the material properties between the ultrasound generator 20 and the point of measurement (at the AFM tip). Alternatively, the ultrasound generator 20 may be positioned elsewhere.

In the embodiment shown, the laser 13 sends a light beam "L" at a position on the AFM cantilever 12. Vibrational movement of the AFM cantilever 12 causes deflection of the reflected beam which is measure by sensor 14 which is sensitive to the position of the impinging beam, e.g. a quadrant detector. The sensor 14 results in a measurement signal S2.

In one path, high frequency components of the signal S2 are extracted by a high pass filter 34 to the analysis system 30. In particular, the passed signal comprises a frequency component with a certain amplitude "A" at the modulation frequency "fm". The amplitude "A" may be retrieved e.g. by a demodulator 35 using the original modulation frequency "fm" as reference. For example, the demodulator 35 may comprise a lock-in amplifier. The amplitude "A" may be processed by a processor 36 to calculate the contact stiffness Kc. The contact stiffness may be used by processor 15 to calculate the damage parameter Sd. Of course the processors 36 and 15 may also be integrated. Alternatively, or in addition, the step of calculating the contact stiffness Kc may omitted and the damage parameter Sd directly calculated from the vibrational amplitude A. Alternatively, or in addition, the contact stiffness Kc may be directly equated a to the damage parameter Sd.

In another path, low frequency components of the signal S2 are extracted by a low pass filter 37 as a measure of a distance or height "Z" between the AFM tip over the substrate surface. The measured distance may be fed into a comparator 38 together with a desired distance "ZO", e.g. corresponding to a desired average force/deflection of the probe 10. The output signal of the comparator may be used to control a height of the scan head 39 to which the probe 10 is attached.

While the present embodiment shows ultrasound waves being applied via the substrate, ultrasound AFM can also be done via tip, or a combination. Accordingly, various embodiments can be envisaged such as heterodyne force microscopy, atomic force acoustic microscopy, waveguide ultrasonic force microscopy, force modulation microscopy. Also, the ultrasound can be generated in various ways such using piezo transducers, electrostatic actuation, photo thermal actuation (e.g. via the light beam "L"), etc.

Figure 4:
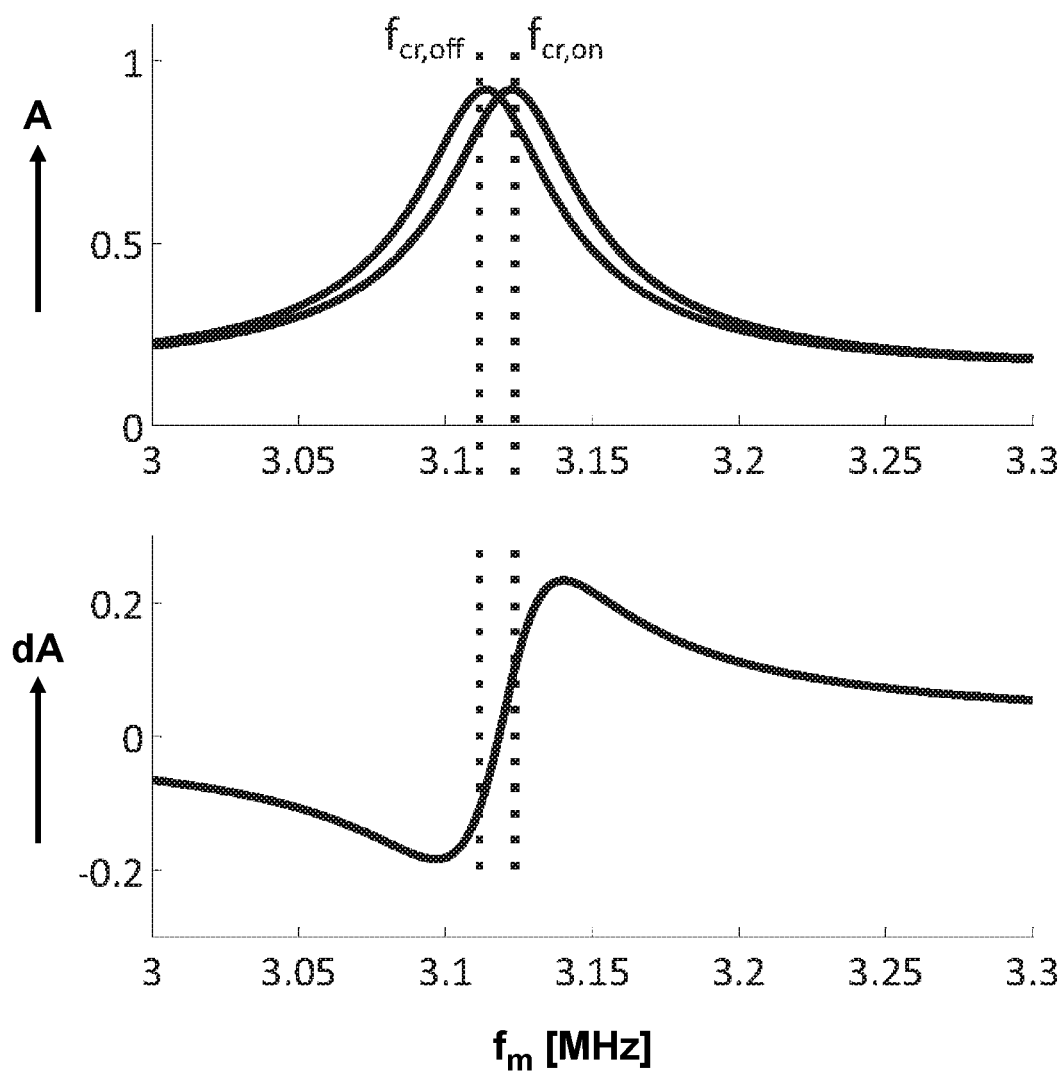
FIG. 4 schematically shows curves indicative of vibrational amplitude depending on a contact resonance frequency.

FIG. 4 schematically shows curves indicative of a vibrational amplitude "A" depending on a proximity between the modulation frequency "fm" and the contact resonance frequency "fcr".

As shown, the modulation frequency "fm" near the contact resonance frequency "fcr" causes an amplitude increased of the AFM cantilever 12 vibrations. For example the amplitude may increase by a factor of two or more compared to an off-resonant vibration of the AFM cantilever 12. In one embodiment, a position of the contact resonance frequency shifts depending whether the AFM tip contacts an exposure area of the electron beam ("fcr,on") or an unexposed area of the substrate ("fcr,off"). As shown in the bottom curve, at certain modulation frequencies, such shifting of the contact resonance frequency "fcr" causes an amplitude difference "dA" of the (cantilever) vibrations caused by the ultrasound waves between the exposure area 1a and the unexposed area 1b. In one embodiment, the amplitude difference "dA" is be used for calculating the damage parameter.

For the purpose of clarity and a concise description, features are described herein as part of the same or separate embodiments, however, it will be appreciated that the scope of the invention may include embodiments having combinations of all or some of the features described. For example, while embodiments were shown for AFM contact force measurements and/or ultrasound AFM, also alternative ways may be envisaged by those skilled in the art having the benefit of the present disclosure for measuring chemical and/or mechanical material properties. For example, other AFM techniques may be employed such as quantitative nano-mechanical (QNM) or peak force mapping. Optical, mechanical, anchor electrical components may be combined or split up into one or more alternative components. It is appreciated that this disclosure offers particular advantages to measuring electron beam damage, and in general can be applied for measuring also other types of damage. The methods as described herein are preferably applied in contact-mode type AFM. It may however also be applied using other modes such as tapping mode, although in tapping mode the duration of periodic contact moments is relatively short and proper filtering of disturbances may be needed.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. A method for measuring a damage of a substrate caused by an electron beam, the method comprising:
providing, using an atomic force microscope (AFM) that includes an AFM cantilever, an AFM tip, and an ultrasound generator, a measurement of at least one material property of the substrate at an exposure area of the electron beam,
wherein the at least one material property is taken from the group consisting of:
a mechanical material property, and
a chemical material property;
wherein a contact resonance frequency of the AFM cantilever while the AFM tip contacts the substrate is a measure for the at least one material property, and
wherein the ultrasound generator is configured to apply ultrasound waves to the substrate that are modulated by a modulation frequency near the contact resonance frequency; and
calculating a damage parameter indicative of the damage based on the measurement of the at least one material property at the exposure area.

2. The method according to claim 1, wherein the at least one material property is taken from the group consisting of:
an adhesive material property, and
a viscoelastic material property.

3. The method according to claim 1, wherein, during the calculating, the damage parameter is calculated based on a comparison of the at least one material property at the exposure area with corresponding at least one reference property measured at an unexposed area, where the unexposed area is an area at which the electron beam has not interacted with the substrate.

4. The method according to claim 1, further comprising determining a damage severity by comparing the damage parameter with a predetermined threshold difference between at least one of the material properties of the exposure area and corresponding reference material properties.

5. The method according to claim 1, wherein the damage parameter is calculated based on at least one of the group consisting of:
an elasticity or stiffness of the exposure area;
an adhesive property of the exposure area;
a deformation property of the exposure area;
a peak force property of the exposure area; and
a viscosity or energy dissipation property of the exposure area.

6. The method according to claim 1, wherein, during the providing a measurement, the atomic force microscope measures subsurface material properties below an exposure area of the substrate, and the at least one material property is a subsurface material property.

7. The method according to claim 1, wherein, during the providing a measurement, ultrasound waves in the substrate are coupled via the AFM tip to the AFM cantilever causing vibration of the AFM cantilever,
wherein a vibrational amplitude of the AFM cantilever depends on a contact stiffness of the AFM tip contacting the substrate, and
wherein the damage parameter is based on a measurement of the vibrational amplitude of the AFM cantilever.

8. The method according to claim 1, wherein the modulation frequency near the contact resonance frequency causes an amplitude increase of the AFM cantilever vibrations by a factor of two or more compared to an off-resonant vibration amplitude of the AFM cantilever.

9. The method according to claim 1, wherein the contact resonance frequency shifts depending whether the AFM tip contacts an exposure area of the electron beam or an unexposed area of the substrate,
wherein a shifting of the contact resonance frequency causes an amplitude difference of the cantilever vibrations caused by the ultrasound waves between the exposure area and the unexposed area, and
wherein the amplitude difference is used for calculating the damage parameter.

10. The method according to claim 1, further comprising:
performing metrology or inspection by means of an electron beam directed at the exposure area of the substrate;

measuring any damage of the substrate caused by the electron beam at the exposure area;
comparing the measured damage to a threshold; and
keeping or discarding the substrate depending on the comparison.

11. A system for measuring a damage of a substrate caused by an electron beam, the system comprising:
an atomic force microscope configured to provide a measurement of at least one material property of the substrate at an exposure area of the electron beam, wherein the measurement is at least one of:
a measurement of a force-distance curve at the exposure area of the electron beam, and
a measurement of a contact stiffness of the atomic force microscope at the exposure area of the electron beam; and
wherein the at least one material property is taken from the group consisting of:
a mechanical material property, and
a chemical material property;
a processing device configured to calculate a damage parameter indicative of the damage based on the measurement of the at least one material property at the exposure area; and
a feedback device configured to output the damage parameter:,
wherein the atomic force microscope includes an ultrasound generator configured to couple ultrasound waves via an AFM tip to an AFM cantilever causing vibration of the AFM cantilever;
wherein a contact resonance frequency of the AFM cantilever while the AFM tip contacts the substrate is a measure for the at least one material property of the substrate, and
wherein the ultrasound generator is configured to modulate the ultrasound waves by a modulation frequency near the contact resonance frequency of the AFM.

12. The system according to claim 11, wherein the processing device is configured to calculate the damage parameter based on a measurement of a vibrational amplitude of the AFM cantilever.

13. The system according to claim 11, wherein the atomic force microscope is configured to provide the measurement of the contact stiffness at the exposure area of the electron beam, and at an unexposed area of the substrate,
wherein the contact resonance frequency shifts depending whether the AFM tip contacts the exposure area or the unexposed area,
wherein a shifting of the contact resonance frequency causes an amplitude difference of the cantilever vibrations caused by the ultrasound waves between the exposure area and the unexposed area; and
wherein the processing device is configured to calculate the damage parameter based on the amplitude difference of the cantilever vibrations caused by the ultrasound waves between the exposure area and the unexposed area.

* * * * *